United States Patent [19]
Renfrew

[11] Patent Number: 5,507,934
[45] Date of Patent: Apr. 16, 1996

[54] APPARATUS FOR PREPARING GELS FOR USE IN ELECTROPHORETIC SEPARATIONS AND SIMILAR APPLICATIONS

[75] Inventor: John A. Renfrew, Burlington, Canada

[73] Assignee: Visible Genetics Inc., Toronto, Canada

[21] Appl. No.: 332,892

[22] Filed: Nov. 1, 1994

[51] Int. Cl.$^6$ .................. G01N 27/26; G01N 27/447
[52] U.S. Cl. .................. 425/174; 204/616; 204/620
[58] Field of Search .................. 204/299 R, 182.8, 204/180.1

[56] References Cited

U.S. PATENT DOCUMENTS

| | | | |
|---|---|---|---|
| 4,704,198 | 11/1987 | Ebersole et al. | 204/182.8 |
| 4,790,919 | 12/1988 | Baylor, Jr. | 204/182.8 |
| 4,811,218 | 3/1989 | Hunkapiller | 364/413.01 |
| 4,823,007 | 4/1989 | Hanson | 250/327.2 |
| 4,834,854 | 5/1989 | Sugihara et al. | 204/182.8 |
| 4,840,756 | 6/1989 | Ebersole et al. | 264/22 |
| 4,844,786 | 7/1989 | Sugihara et al. | 204/299 R |
| 4,863,647 | 9/1989 | Baylor, Jr. | 264/22 |
| 4,929,329 | 5/1990 | Danby et al. | 204/299 R |
| 4,971,677 | 11/1990 | Kambara et al. | 204/299 R |
| 4,985,128 | 1/1991 | Ebersole et al. | 204/182.8 |
| 5,047,135 | 9/1991 | Nieman | 204/299 R |
| 5,062,942 | 11/1991 | Kambara et al. | 204/299 R |
| 5,069,769 | 12/1991 | Fujimiya et al. | 204/182.81 |
| 5,069,773 | 12/1991 | Frangioni | 204/299 R |
| 5,071,531 | 12/1991 | Soane | 204/182.8 |
| 5,091,652 | 2/1992 | Mathies et al. | 250/458.1 |
| 5,092,973 | 3/1992 | Zare et al. | 204/182.1 |
| 5,119,316 | 6/1992 | Dam et al. | 364/498 |
| 5,122,345 | 6/1992 | Tabor et al. | 422/116 |
| 5,164,066 | 11/1992 | Yetman et al. | 204/299 R |
| 5,186,807 | 2/1993 | Sanford et al. | 204/299 R |
| 5,192,412 | 3/1993 | Kambara et al. | 204/299 R |
| 5,209,831 | 5/1993 | MacConnell | 204/299 R |
| 5,228,971 | 7/1993 | Brumley, Jr. et al. | 204/299 R |
| 5,306,404 | 4/1994 | Notsu | 204/182.8 |
| 5,338,426 | 8/1994 | Shigeura et al. | 204/299 R |
| 5,365,455 | 11/1994 | Tibbetts et al. | 364/497 |

OTHER PUBLICATIONS

Current Protocols in Molecular Biology, Section 10.2.1–10.2.21, John Wiley & Sons (1991).

Primary Examiner—John Niebling
Assistant Examiner—John S. Starsiak, Jr.
Attorney, Agent, or Firm—Oppedahl & Larson

[57] ABSTRACT

An apparatus for the rapid filling and polymerization of electrophoresis gels comprises:
  (a) a housing;
  (b) a filling fixture removably disposed within the housing and adapted to receive a gel holder having an internal gel compartment;
  (c) an injection system, which is connectible to a reservoir for holding a polymerizable solution;
  (d) a solution injection connector adapted to couple the injection system to a gel holder placed within the filling fixture,
  (e) a controller for the injection system, which causes the injection system to inject polymerizable solution from the reservoir into the gel compartment; and
  (f) a radiation source disposed within the housing in a location effective to irradiate polymerizable solution within the gel compartment of a gel holder in the filling fixture. The filling fixture may be mounted on a base which is slidable between a position inside the housing, and a position outside the housing to permit easy placement of a gel holder into the filling fixture.

15 Claims, 4 Drawing Sheets

APPARATUS FOR PREPARING GELS FOR USE IN ELECTROPHORETIC SEPARATIONS AND SIMILAR APPLICATIONS

BACKGROUND OF THE INVENTION

This application relates to an apparatus for preparing gels, particularly polyacrylamide gels, for use in electrophoretic separation of biomolecules and similar applications.

Polyacrylamide gel electrophoresis (PAGE) separation of biomolecules is now routinely performed. *Current Protocols in Molecular Biology*, Chap. 10, John Wiley & Sons, (1994). A polyacrylamide gel provides a suitably insoluble sieve that separates biomolecules in solution by size and conformation as they are drawn through the sieve under electromotive force. Such separation of biomolecules provides valuable insights into their structures and functions. For example, PAGE separation can separate two polypeptides of the same size but of different isoforms or polypeptides only 100 daltons difference in size (Current Protocols, 1994). Another use for PAGE is in separation of nucleic acids based on size of fragments, such as in the extremely important application of DNA sequence determination. Maniatis et al., *Molecular Cloning: A Laboratory Manual*, 2nd ed., Chap. 13 (1987).

The prior art on PAGE is extensive. Many patents and scientific papers disclose uses for PAGE in research applications. DNA sequencing may be carried out using automated systems designed for laboratory application. These techniques have historically been important for sequencing long stretches of unknown DNA, such as is the focus of the Human Genome Project. Methods and apparatus for sequencing of DNA are described in U.S. Pat. Nos. 4,811,218; 4,823,007; 5,062,942; 5,091,652; 5,119,316; 5,122,345; 5,228,971, and 5,338,426 which are incorporated herein by reference.

Unfortunately, the traditional techniques for preparation of gels for use in electrophoresis are inadequate for use in clinical diagnostic services, such as the emerging field of clinical diagnostic DNA sequencing. For clinical diagnostic DNA sequencing purposes, it is desirable to sequence hundreds of DNA sequences per day. Existing methods do not provide for such capacity. For example, typical methods of DNA sequencing require that a skilled technician spend up to four hours constructing a gel holder, filling the gel holder with actively polymerizing acrylamide solution, inserting a well-forming comb before substantial polymerization has occurred, and then waiting for the gel to polymerize. (U.S. Pat. No. 5,338,426; U.S. Pat. No. 5,069,773; Maniatis, 1987.) Using the gel is equally cumbersome. Loading sample to be electrophoresed requires painstaking care to ensure the integrity of loading wells and to prevent samples from running together. Thus, in order to make maximum clinical use of the opportunities presented by our ever increasing knowledge of the human genetics and the genetic causes of many disease, it would be advantageous to have a method of rapidly making polyacrylamide gels which are convenient for more efficient sample loading and running, particularly for use in clinical diagnostic applications.

It is an object of the invention to provide an apparatus for filling a gel holder with a polymerizable solution, and catalyzing the polymerization of the solution using ultraviolet light to form a gel usable for electrophoretic separation of biomolecules, particularly nucleic acids.

It is a further object of the invention to provide an apparatus for the rapid and convenient formation of gels which are more easily loaded with sample.

SUMMARY OF THE INVENTION

These and other objects are achieved using an apparatus specifically designed for the rapid filling and polymerization of electrophoresis gels. This apparatus comprises:

(a) a housing;

(b) a filling fixture removably disposed within the housing and adapted to receive a gel holder having an internal gel compartment;

(c) an injection system, which is connectible to a reservoir for holding a polymerizable solution;

(d) a solution injection connector adapted to couple the injection system to a gel holder placed within the filling fixture, (e) a controller for the injection system, which causes the injection system to inject polymerizable solution from the reservoir into the gel compartment; and (f) a radiation source disposed within the housing in a location effective to irradiate polymerizable solution within the gel compartment of a gel holder in the filling fixture. In a preferred embodiment of the apparatus, the filling fixture is mounted on a base which is slidable between a position inside the housing, and a position outside the housing to permit easy placement of a gel holder into the filling fixture.

DETAILED DESCRIPTION OF THE INVENTION

Figure 1:
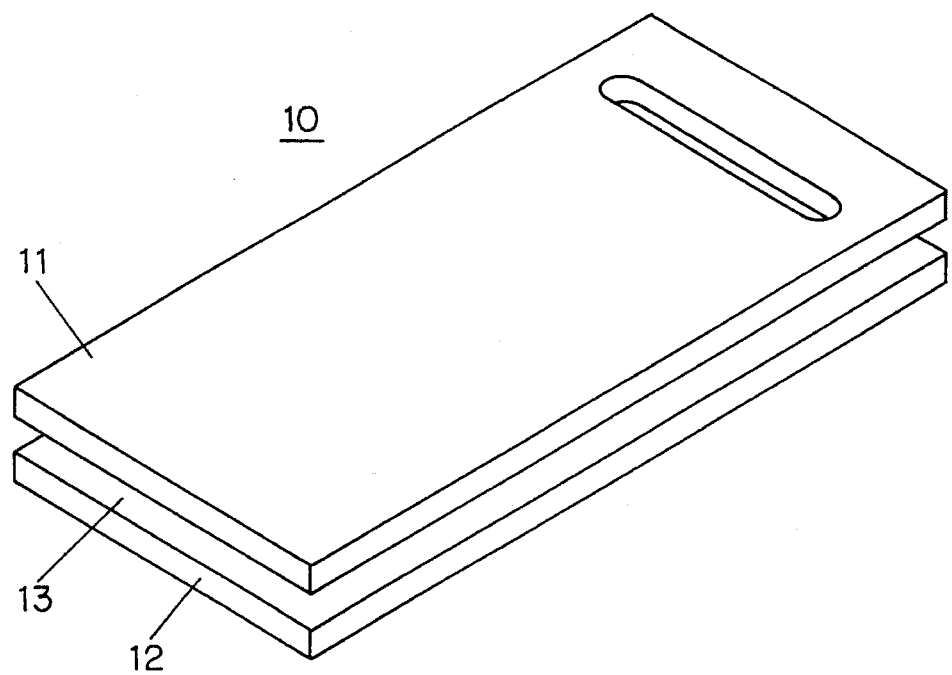
FIG. 1 shows a gel holder which may be filled and polymerized using the method and apparatus of the invention.

The present invention provides an apparatus for the filling of a pre-formed gel holder, and for the polymerization of the gel within the holder. In general, gel holders 10 which can be filled and polymerized in the apparatus of the invention will have a top substrate 11 and a bottom substrate 12 held together with a defined spacing to form an internal gel compartment 13. (FIG. 1) Preferred gel holders are those described in concurrently filed U.S. patent application Ser. No. 08/332,577, which is incorporated herein by reference.

Figure 2:
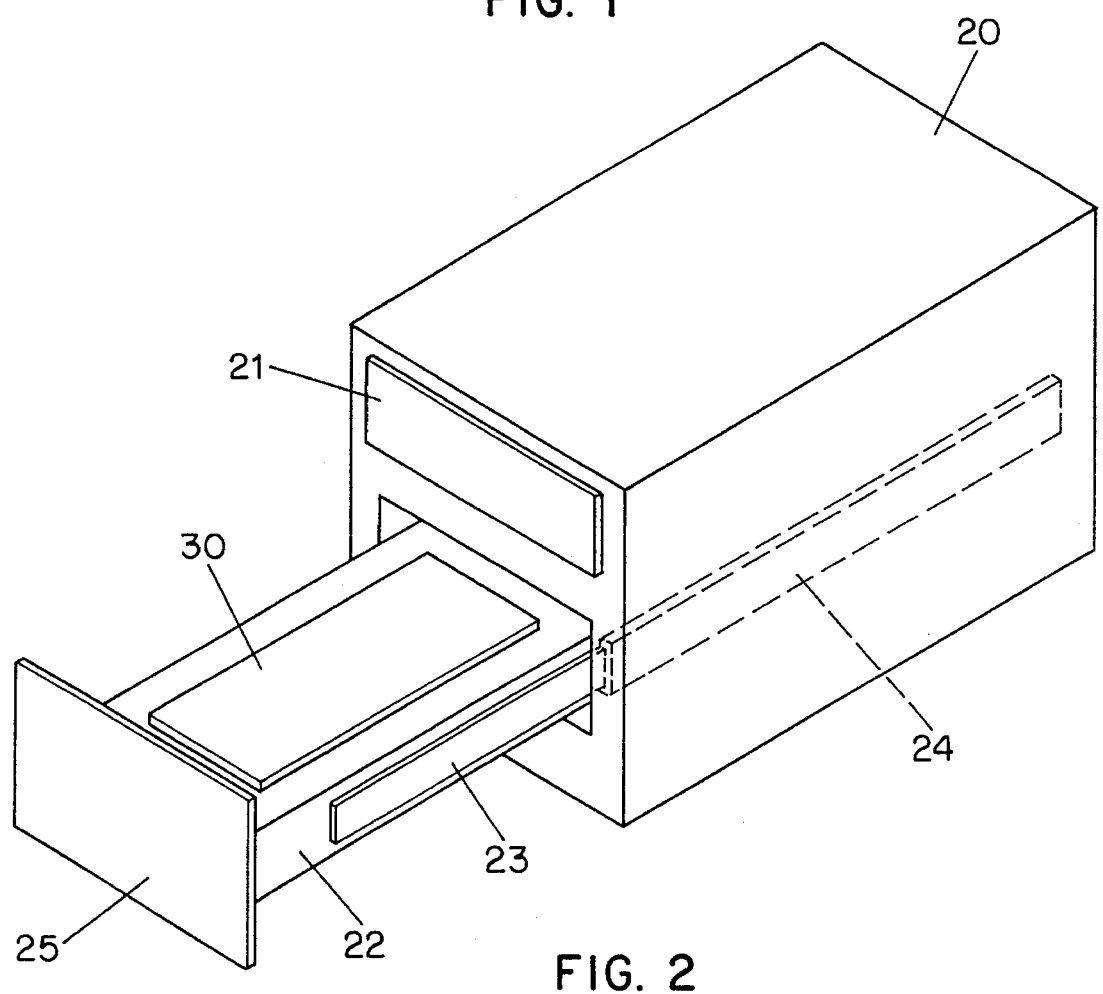
FIG. 2 shows an exterior view of an apparatus according to the invention.

FIG. 2 shows an exterior view of an apparatus in accordance with the invention. As indicated, the apparatus is disposed within a housing 20. Inside the housing is a radiation source such as an ultraviolet lamp for use in initiating polymerization of the gel. A control panel 21 and a sliding drawer unit 22 are positioned on a front face of the housing 20. Tracks 23 are attached at on sides of the drawer unit 22. The tracks 23 fit into sliding track guides 24 (shown in phantom in FIG. 2) mounted on each side inside the housing 20. At its full extension, the sliding tracks 23 are retained in the sliding track guides 24 by track stops (not shown). At its full retraction the sliding of the drawer is stopped by contact of the face 25 of the drawer with the housing 20. Any sliding means with low coefficient of friction may be employed to bear the weight of the drawer, such as ball bearings, Teflon, wheels or rubber.

Figure 3A:
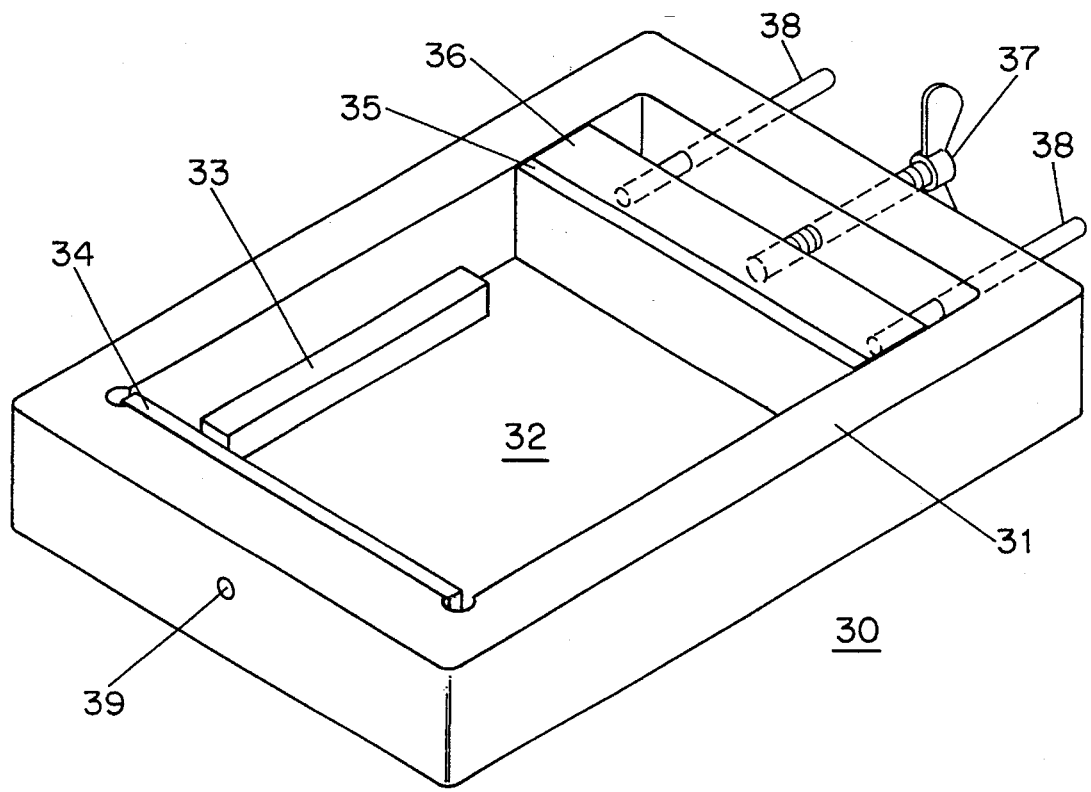
FIGS. 3A and B shows a filling fixture for use in accordance with the invention.
Figure 3B:
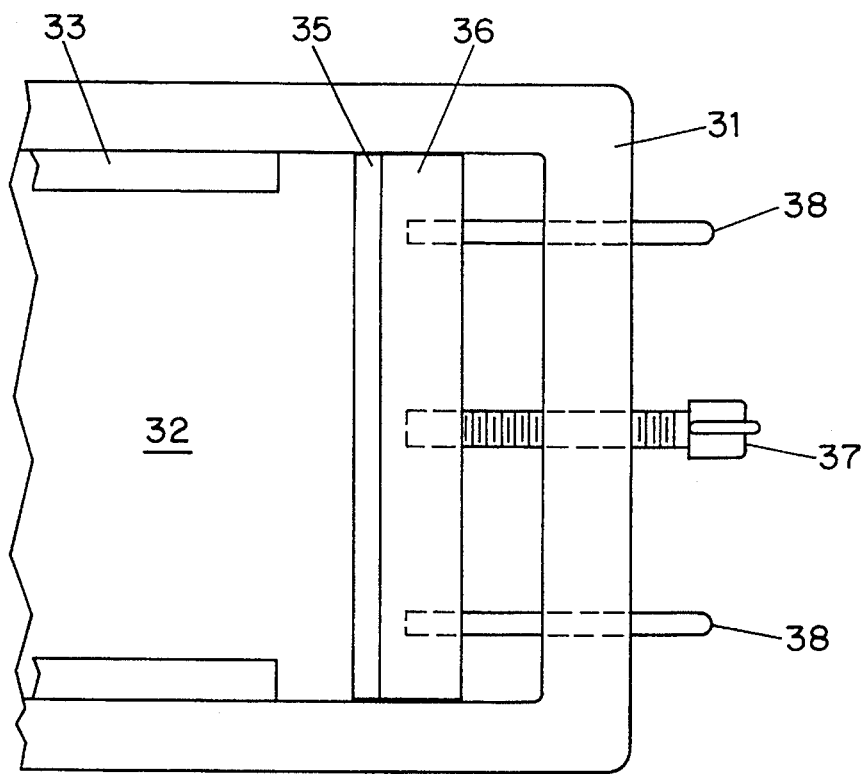
Figure 4:
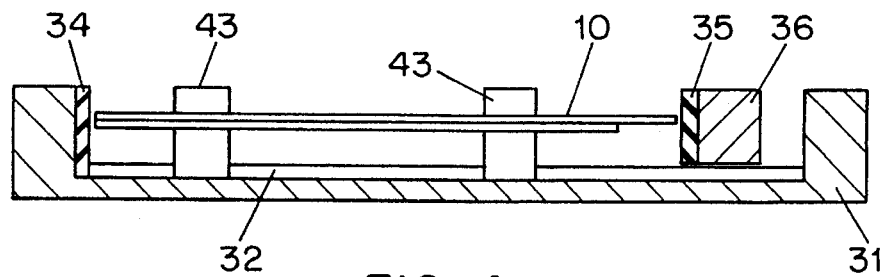
FIG. 4 shows a side sectional view of a filling fixture for use in accordance with the invention having a gel holder positioned therein.

The drawer unit 22 supports a filling fixture 30 such as that shown in FIGS. 3A, 3B and 4. The filling fixture 30 has a rectangular frame 31 surrounding a central base region 32 sized to receive a gel holder. The gel holder rests over the central base region 32 and is supported underneath along each side by a narrow (~3 mm) ledge 33 protruding from the filling fixture. Alternatively, the gel holder 10 may be supported by and held between support members 43 running across the central base region 32 as shown in FIG. 4.

When first placed in the filling fixture, the open end of the microgel holder loosely contacts a silicon strip 34 at the bottom of the filling fixture 30. At the top of the filling fixture, a silicon strip 35 attached to an adjustable bar 36 running widthwise at the top of the filling fixture 30 loosely contacts the top end of the gel holder. By means of a screw 37 or other force directing means, such as a lever, the silicon strip 35 on the moveable bar 36 is placed in close contact with the top of the gel holder and the bottom of the gel holder is thereby secured in close, sealing contact with the silicon strips 34 and 35 at the bottom and top of the filling fixture 30. Fixed guide bolts 38 which slide within openings in the frame 31 ensure that the moveable bar 36 is stabilized and directed smoothly in the direction of the force of the screw 37.

Figure 5:
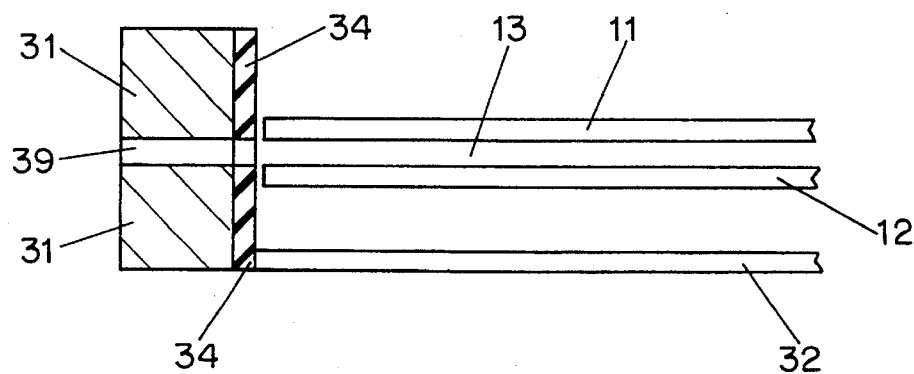
FIG. 5 shows a detailed view of the connection between the injection system and the gel holder.

The bottom end of the filling fixture 30 and the silicon strip 34 have an injection port 39 passing through them. When the gel holder is properly secured in the filling fixture 30, the injection port 39 is aligned with the open bottom edge of the gel holder 10 as shown in FIG. 5, providing a pathway for injection of a polymerizable solution into the gel compartment 13 of the gel holder 10. Thus, the silicon strip 34 serves as a solution injection connector and is adapted to couple the injection system to a gel holder placed within the filling fixture.

When the microgel holder is secured in the filling fixture it is ready to be filled and polymerized. Filling and polymerization takes place inside the housing 20. The drawer unit 22 containing gel holder 10, in the filling fixture 30, is slid inwards into the housing 20. In a preferred embodiment of the invention, closing the drawer starts an automated filling and curing process in which polymerizable solution is pumped into the gel holder, and an ultraviolet light disposed within the housing 20 over the gel holder is activated to initiate the polymerization reaction.

Figure 6:
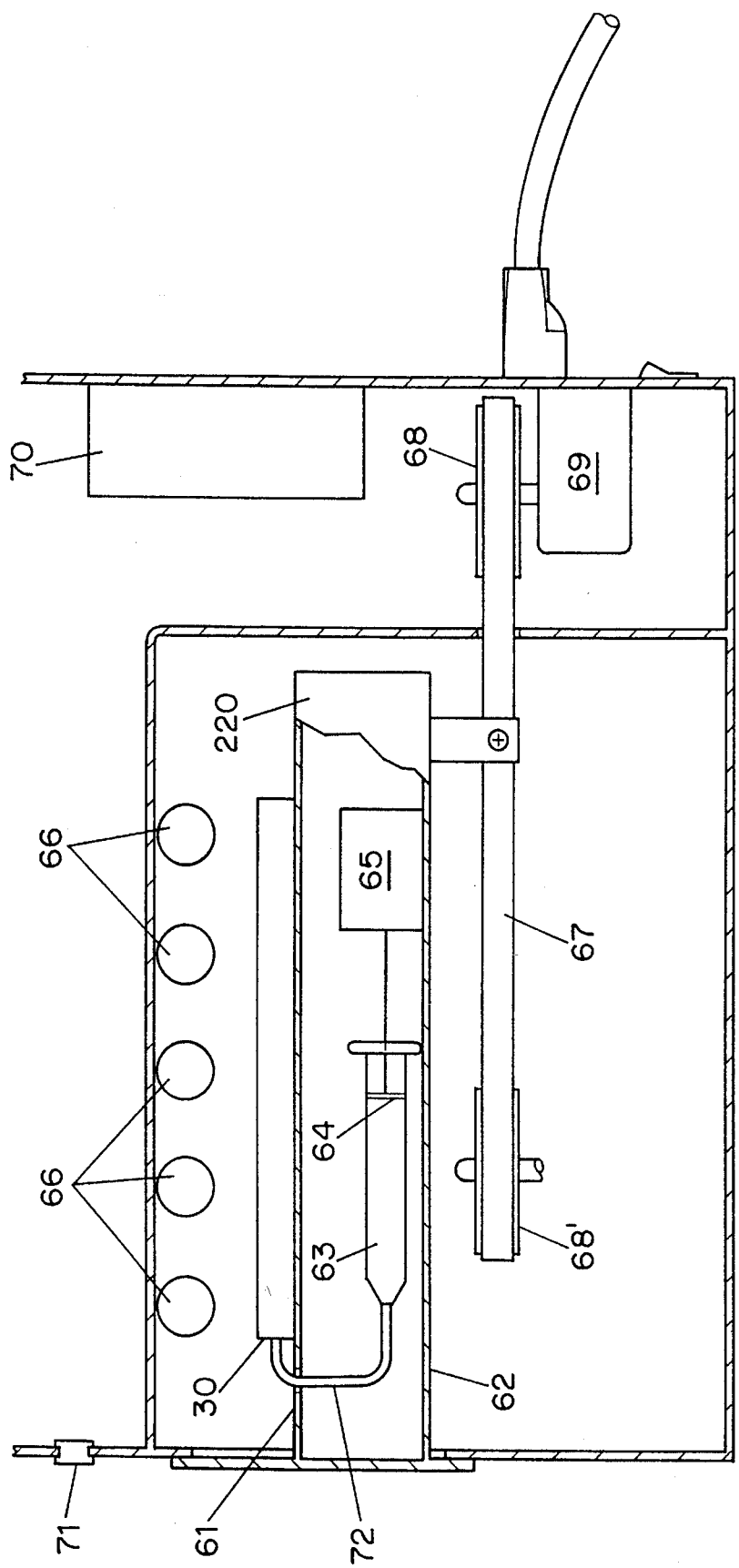
FIG. 6 shows a cross-sectional view of an embodiment of the invention.

FIG. 6 shows a cross-sectional view of one embodiment of the invention in which a two level drawer unit 220 is utilized. As shown, the filling fixture 30 with the gel holder disposed therein is disposed on the upper shelf 61 of the drawer unit 220. A lower shelf 62 supports the solution injection system which is connected to the solution injection port of the top shelf by a tube 72.

The solution injection system comprises a canister 63 of gel forming solution. The solution employed may be an acrylamide solution, with or without urea or sodium dodecyl sulphate (SDS), and with or without any other chemical additives, alternatively it may be any non-acrylamide monomer which exists in solution at or around room temperature and can be polymerized in the presence of ultraviolet light, either with or without further additives.

The canister 63 contains a plunger 64 operatively connected to a motor 65. When the motor is activated, the plunger 64 is driven by the dedicated motor 65 for a predetermined period of time to dispense the correct amount of gel forming solution into the gel holder. In addition, fan 70 may be turned on at the motor to provide venting and heat dissipation inside the housing as part of the process of starting the filling and polymerization cycle, or it may be activated separately.

The injected solution flows evenly through the gel compartment, filling the compartment. Air escapes from the gel compartment through the openings in the window of the top substrate. After the gel compartment has been filled, UV lamps 66 disposed in the top of the housing are activated for a period of time sufficient to polymerize the gel in the holder. For example, using five 20 Watt UVA lamps an acrylamide solution in a gel holder will be fully polymerized in about 5 to 10 minutes. The apparatus then shuts off the lamps and signals completion of the cycle, for example by opening the drawer unit, by sounding an audible alarm or by lighting a signal light.

Activation of the motor 65 to start the gel filling and polymerization cycle can be accomplished by any of several means. First, the cycle can be initiated in response to a command or series of commands entered through the control panel 21 on the front of the housing 20, or the activation of a "start" switch. In the simplest embodiment of the invention, each phase of the processing is started separately by an operator. Thus, a command is entered to start the filling process, and then a second command is entered after the filling process is complete to energize the lamps inside the housing and begin the polymerization part of the cycle.

Preferably, the apparatus will include a mechanism for the controlling the performance of a complete filling and polymerization cycle in response to a single initiation signal. Thus, for example, the apparatus may include a user interface circuit board ("UI Circuit Board") which automatically coordinates the filling/polymerization cycle. The UI Circuit Board is connected to a microprocessor which controls the motor 65 for gel filling, and the illumination of the ultraviolet lamps 66. Upon activation of a switch on the UI Circuit Board, the microprocessor activates the motor 65 for a predetermined but adjustable period of time. The adjustment of this time interval may be presented to the user as a time interval or as an adjustment in the volume of polymerizable solution to be transferred. The motor 65 is then turned off by the microprocessor, and the lamps 66 are energized for a predetermined but user adjustable period of time.

The UI Circuit Board may contain a further switch or switches for controlling the motor 65. A first such switch would allow for replacement of the canister 63 by fully retracting the plunger 64 from the canister. A second switch could allow for manual control of the motor 65, for example to permit priming of the solution injection system after replacement of the canister 63.

As an alternative to the use of a switch on the exterior of the housing, a filling/polymerization cycle can be started automatically upon closure of the drawer unit. For example, a switch may be placed such that it is automatically actuated when the drawer unit is closed. In this case, it is advantageous to place an sensor switch in the filling fixture 30 such that the mechanism can only operate when a gel holder is installed in the fixture.

The apparatus shown in FIG. 6 further shows a reversible belt 67 attached to the drawer unit 22. The belt 67 is supported by a driven and an undriven pulley 68 and 68'. The driven pulley 68 is connected to motor 69, which in turn is connected to a switch 71 on the front of the housing. The motor 69 extends the drawer or retracts the drawer in response to the position of switch 71. The activation of this switch to retract the drawer may also initiate the filling/polymerization cycle.

While the invention has been described with above with reference to the formation of polyacrylamide gels crosslinked using ultra-violet light as an initiator, it will be understood that the invention can also be used with other initiator systems and radiation sources. For example, if the cross-linking is achieved with a thermal initiator such as TEMED, IR lamps may be used as the radiation source 66. Visible light sources might also be used if a suitable light absorber which can transfer energy to activate the acrylamide is included in the gel.

After polymerization, the polymerized microgel in the microgel holder is removed from the filling fixture by unscrewing or unclamping the microgel holder. The microgel is now ready to mounted on a gel running apparatus and loaded with sample to be electrophoresed on the gel.

EXAMPLE

Figure 7:
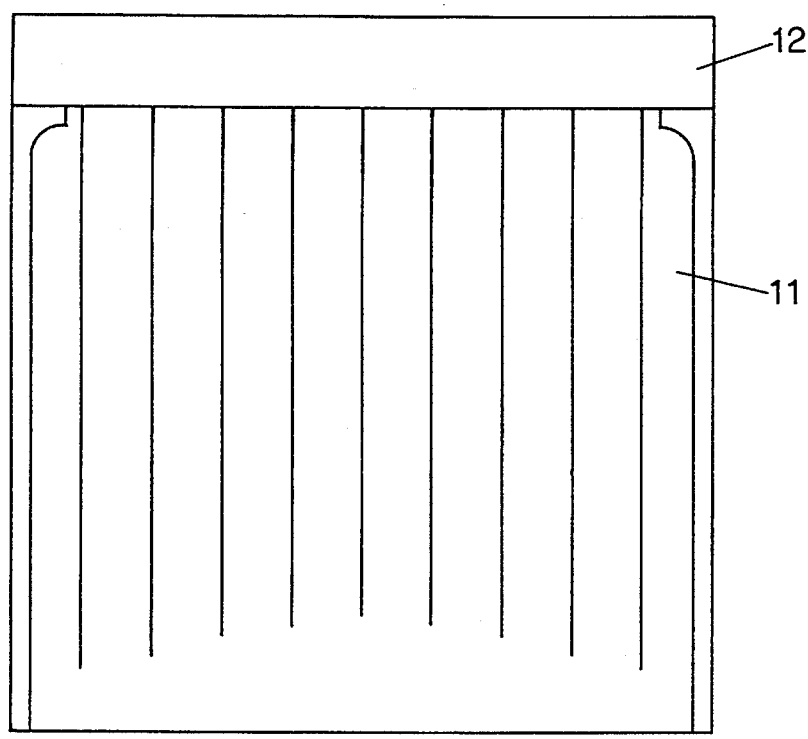
FIG. 7 shows a top view of a gel holder for use in accordance with the invention.

A UV activated adhesive matrix was prepared using Minico® M07950-R acrylate adhesive from Emerson & Cuming Inc., Woburn, Mass., mixed with 2% by weight Sigma® glass beads (106 micron and finer) filtered to select beads of a size of 45 to 53 microns. The adhesive matrix was screen printed onto the bottom substrate 12 in the pattern shown in FIG. 7. The top substrate 11 was then positioned on top of the bottom substrate 12. The substrates were then exposed to 20 Watts UVA light (wavelength 315–385 nm) to initiate curing of the adhesive and to bond the two substrates together.

After the adhesive was cured, the gel holder was placed horizontally in a filling fixture in accordance with the invention and placed into the top shelf of a device as shown in FIG. 6. A first switch on the UI Circuit Board was manually activated which initiated retraction of the drawer into the housing. Upon full retraction of the drawer, a second switch on the UI Circuit Board was manually activated to commence the filling/polymerization cycle. A polyacrylamide gel forming solution containing 6% acrylamide (19:1 bis-acrylamide), 7M urea in 0.6×TBE and 10 ppm riboflavin was driven into the gel holder, which was then exposed to ultraviolet light from five 20 W UVA-lamps disposed on the interior of the housing for 10 minutes to polymerize the gel.

I claim:

1. An apparatus for polymerizing a gel, comprising
   (a) a housing;
   (b) an injection system, said injection system connectible to a reservoir for holding a polymerizable solution;
   (c) a filling fixture removably disposed within the housing and adapted to receive a gel holder having an internal gel compartment;
   (d) a solution injection connector adapted to couple the injection system to a gel holder placed within the filling fixture,
   (e) a controller for the injection system, which causes the injection system to inject polymerizable solution from the reservoir into the gel compartment; and
   (f) a radiation source disposed within the housing in a location effective to irradiate polymerizable solution within the gel compartment of a gel holder in the filling fixture.

2. An apparatus according to claim 1, wherein the filling fixture is disposed on a drawer slidably disposed within the housing.

3. An apparatus according to claim 2, wherein the drawer has an upper shelf and a lower shelf, and wherein the filling fixture is disposed on the upper shelf and the injection system is disposed on the lower shelf.

4. An apparatus according to claim 3, wherein the injection system includes a reservoir for polymerizable solution disposed on the lower shelf.

5. An apparatus according to claim 2, further comprising a motor operatively connected to the drawer for retracting and extending the drawer.

6. An apparatus according to claim 1, wherein the radiation source irradiates the polymerizable solution with ultraviolet radiation.

7. An apparatus according to claim 6, wherein the filling fixture is disposed on a drawer slidably disposed within the housing.

8. An apparatus according to claim 7, wherein the drawer has an upper shelf and a lower shelf, and wherein the filling fixture is disposed on the upper shelf and the injection system is disposed on the lower shelf.

9. An apparatus according to claim 8, wherein the injection system includes a reservoir for polymerizable solution disposed on the lower shelf.

10. An apparatus according to claim 7, further comprising a motor operatively connected to the drawer for retracting and extending the drawer.

11. An apparatus according to claim 1, wherein the controller is connected to a switch, and wherein activation of the switch initiates a cycle of filling the gel holder with polymerizable solution and irradiating the gel holder to polymerize the polymerizable solution.

12. An apparatus according to claim 11, wherein the filling fixture is disposed on a drawer slidably disposed within the housing.

13. An apparatus according to claim 12, further comprising a motor operatively connected to the drawer for retracting and extending the drawer relative to the housing.

14. An apparatus according to claim 13, wherein activation of the switch causes the drawer to be retracted into the housing at the beginning of the cycle and extended from the housing at the end of the cycle.

15. An apparatus according to claim 11, wherein the radiation source irradiates the polymerizable solution with ultraviolet radiation.

\* \* \* \* \*